(12) United States Patent
Strumolo

(10) Patent No.: US 9,208,289 B2
(45) Date of Patent: Dec. 8, 2015

(54) VEHICLE SYSTEM REACTION TO MEDICAL CONDITIONS

(71) Applicant: Ford Global Technologies, LLC, Dearborn, MI (US)

(72) Inventor: Gary Steven Strumolo, Beverly Hills, MI (US)

(73) Assignee: FORD GLOBAL TECHNOLOGIES, LLC, Dearborn, MI (US)

( * ) Notice: Subject to any disclaimer, the term of this patent is extended or adjusted under 35 U.S.C. 154(b) by 0 days.

(21) Appl. No.: 14/191,914

(22) Filed: Feb. 27, 2014

(65) Prior Publication Data

US 2014/0179256 A1   Jun. 26, 2014

Related U.S. Application Data

(63) Continuation of application No. 12/941,483, filed on Nov. 8, 2010, now Pat. No. 8,704,669.

(51) Int. Cl.
| | |
|---|---|
| G06F 21/00 | (2013.01) |
| G06F 19/00 | (2011.01) |
| B60H 1/00 | (2006.01) |
| B60K 28/06 | (2006.01) |
| A61B 5/145 | (2006.01) |

(52) U.S. Cl.
CPC ............ *G06F 19/3487* (2013.01); *B60H 1/008* (2013.01); *B60H 1/00771* (2013.01); *B60H 1/00849* (2013.01); *B60K 28/066* (2013.01); *G06F 19/3481* (2013.01); *A61B 5/14532* (2013.01); *B60W 2550/12* (2013.01)

(58) Field of Classification Search
CPC .......................... G06F 19/3487; A61B 5/7475
USPC .............. 340/573.1, 426.11, 426.13, 426.19, 340/438, 439, 539.11, 539.12, 576; 600/300, 301, 365; 701/1; 705/2, 3
See application file for complete search history.

(56) References Cited

U.S. PATENT DOCUMENTS

| | | | |
|---|---|---|---|
| 3,974,350 | A | 8/1976 | Breed |
| 5,365,516 | A | 11/1994 | Jandrell |
| 5,410,739 | A | 4/1995 | Hart |
| 5,465,079 | A | 11/1995 | Bouchard et al. |

(Continued)

FOREIGN PATENT DOCUMENTS

| | | |
|---|---|---|
| CN | 101206462 A | 6/2008 |
| JP | 2004242945 A | 9/2004 |
| WO | 2010055509 A1 | 5/2010 |

OTHER PUBLICATIONS

Google Health, About Google Health, www.healthvault.com, Dec. 20, 2010.

(Continued)

*Primary Examiner* — Van Trieu
(74) *Attorney, Agent, or Firm* — Jennifer M. Stec; Brooks Kushman P.C.

(57) ABSTRACT

A computer-implemented method includes registering at least one medical condition associated with a vehicle occupant. The method also includes monitoring environmental conditions for the onset of a trigger likely to cause complications with regards to the medical condition. The method further includes warning the vehicle occupant about the onset of the trigger. The method also includes adjusting a vehicle component or system, via the VCS, in response to the onset of the trigger.

11 Claims, 4 Drawing Sheets

(56) References Cited

U.S. PATENT DOCUMENTS

| | | | |
|---|---|---|---|
| 5,653,462 A | 8/1997 | Breed et al. |
| 5,686,910 A | 11/1997 | Timm et al. |
| 5,748,473 A | 5/1998 | Breed et al. |
| 5,829,782 A | 11/1998 | Breed et al. |
| 5,845,255 A | 12/1998 | Mayaud |
| 5,848,802 A | 12/1998 | Breed et al. |
| 5,901,978 A | 5/1999 | Breed et al. |
| 6,078,853 A | 6/2000 | Ebner et al. |
| 6,104,296 A | 8/2000 | Yasushi et al. |
| 6,128,482 A | 10/2000 | Nixon et al. |
| 6,272,411 B1 | 8/2001 | Corrado et al. |
| 6,282,475 B1 | 8/2001 | Washington |
| 6,330,499 B1 | 12/2001 | Chou et al. |
| 6,353,785 B1 | 3/2002 | Shuman et al. |
| 6,445,300 B1 | 9/2002 | Luman |
| 6,474,683 B1 | 11/2002 | Breed et al. |
| 6,602,191 B2 | 8/2003 | Quy |
| 6,603,999 B2 | 8/2003 | SerVaas |
| 6,734,799 B2 | 5/2004 | Munch |
| 6,762,684 B1 | 7/2004 | Camhi |
| 6,778,672 B2 | 8/2004 | Breed et al. |
| 6,793,242 B2 | 9/2004 | Breed et al. |
| 6,942,248 B2 | 9/2005 | Breed et al. |
| 6,944,536 B2 | 9/2005 | Singleton |
| 6,945,860 B2 | 9/2005 | Matsui et al. |
| 6,946,966 B2 | 9/2005 | Koenig |
| 7,019,650 B2 | 3/2006 | Volpi et al. |
| 7,027,621 B1 | 4/2006 | Prokoski |
| 7,042,345 B2 | 5/2006 | Ellis |
| 7,050,897 B2 | 5/2006 | Breed et al. |
| 7,164,117 B2 | 1/2007 | Breed et al. |
| 7,266,430 B2 | 9/2007 | Basson et al. |
| RE39,871 E | 10/2007 | Skardon |
| 7,301,464 B2 | 11/2007 | Coulter |
| 7,534,206 B1 | 5/2009 | Lovitt et al. |
| 7,670,288 B2 | 3/2010 | Sher |
| 7,680,690 B1 | 3/2010 | Catalano |
| 7,693,625 B2 | 4/2010 | Bauerle et al. |
| 7,775,453 B2 | 8/2010 | Hara |
| 7,792,701 B2 | 9/2010 | Basson et al. |
| 7,805,224 B2 | 9/2010 | Basson et al. |
| 8,078,334 B2 | 12/2011 | Goodrich |
| 8,104,814 B2 | 1/2012 | Sartin et al. |
| 8,140,358 B1 | 3/2012 | Ling et al. |
| 8,149,111 B2 | 4/2012 | Monroe |
| 8,196,694 B2 | 6/2012 | Biondo et al. |
| 8,207,859 B2* | 6/2012 | Enegren et al. | 340/573.1 |
| 8,207,860 B2* | 6/2012 | Enegren et al. | 340/573.1 |
| 8,229,758 B2 | 7/2012 | Moncrease |
| 8,301,108 B2* | 10/2012 | Naboulsi | 455/345 |
| 8,350,722 B2 | 1/2013 | Tewari et al. |
| 2001/0020902 A1 | 9/2001 | Tamura |
| 2001/0034617 A1 | 10/2001 | Kimata |
| 2001/0039503 A1 | 11/2001 | Chan et al. |
| 2002/0013788 A1 | 1/2002 | Pennell et al. |
| 2002/0099424 A1 | 7/2002 | Ferek-Petric |
| 2002/0118112 A1 | 8/2002 | Lang |
| 2002/0123833 A1 | 9/2002 | Sakurai et al. |
| 2003/0028792 A1 | 2/2003 | Plow et al. |
| 2003/0043045 A1 | 3/2003 | Yasushi et al. |
| 2003/0064748 A1 | 4/2003 | Stulberger et al. |
| 2003/0065432 A1 | 4/2003 | Shuman et al. |
| 2003/0144886 A1* | 7/2003 | Taira | 705/3 |
| 2003/0208409 A1 | 11/2003 | Mault |
| 2004/0046666 A1 | 3/2004 | Yasuchi |
| 2004/0133082 A1 | 7/2004 | Abraham-Fuchs et al. |
| 2005/0125258 A1 | 6/2005 | Yellin et al. |
| 2005/0171660 A1 | 8/2005 | Woolford et al. |
| 2005/0190062 A1 | 9/2005 | Sullivan et al. |
| 2005/0192830 A1 | 9/2005 | Pugh et al. |
| 2006/0008058 A1 | 1/2006 | Dai et al. |
| 2006/0015254 A1 | 1/2006 | Smith |
| 2006/0022834 A1 | 2/2006 | Rosenfeld et al. |
| 2006/0059013 A1 | 3/2006 | Lowe |
| 2006/0161456 A1 | 7/2006 | Baker et al. |
| 2006/0271394 A1 | 11/2006 | Kelly |
| 2006/0290516 A1 | 12/2006 | Muehlsteff et al. |
| 2007/0007067 A1 | 1/2007 | Pollehn et al. |
| 2007/0088624 A1 | 4/2007 | Vaughn et al. |
| 2007/0233384 A1 | 10/2007 | Lee |
| 2008/0033644 A1 | 2/2008 | Bannon |
| 2008/0097552 A1 | 4/2008 | Dicks et al. |
| 2008/0097917 A1 | 4/2008 | Dicks et al. |
| 2008/0218376 A1 | 9/2008 | Dicks et al. |
| 2008/0249386 A1 | 10/2008 | Besterman et al. |
| 2008/0297336 A1 | 12/2008 | Lee |
| 2009/0070148 A1 | 3/2009 | Skocic |
| 2009/0270705 A1* | 10/2009 | Enegren et al. | 600/365 |
| 2009/0292555 A1 | 11/2009 | Brown |
| 2010/0042440 A1* | 2/2010 | Joao | 705/3 |
| 2010/0268051 A1 | 10/2010 | Prasad et al. |
| 2010/0294583 A1 | 11/2010 | Biondo et al. |
| 2010/0324817 A1 | 12/2010 | Hansen et al. |
| 2011/0117878 A1* | 5/2011 | Barash et al. | 455/404.2 |
| 2011/0172550 A1* | 7/2011 | Martin et al. | 600/523 |
| 2011/0193707 A1 | 8/2011 | Ngo |
| 2011/0210867 A1 | 9/2011 | Benedikt |
| 2011/0213625 A1* | 9/2011 | Joao | 705/3 |
| 2011/0218839 A1 | 9/2011 | Shamaiengar |
| 2012/0035962 A1* | 2/2012 | Iliff | 705/3 |
| 2012/0112915 A1 | 5/2012 | Strumolo |
| 2012/0166680 A1 | 6/2012 | Masoud et al. |
| 2012/0171982 A1 | 7/2012 | Schunder et al. |
| 2012/0173336 A1 | 7/2012 | Strumolo |
| 2012/0182143 A1 | 7/2012 | Gaines et al. |
| 2012/0184237 A1 | 7/2012 | Gaines et al. |
| 2012/0185265 A1 | 7/2012 | Kochhar |
| 2013/0096649 A1* | 4/2013 | Martin et al. | 607/60 |

OTHER PUBLICATIONS

Welcome to Microsoft Healthvault, Health Vault, www.google.com/health, Dec. 20, 2010.
WebMD, www.webmd.com, Dec. 20, 2010.
Medical Procedures/Surgical Procedures What's the Cost?, 1st Health Insurance Quotes.conn, printed Oct. 30, 2010.
Kermit Whitfield, "A hitchhiker's guide to the telematics ecosystem", Automotive Design & Production, Oct. 2003, http://findarticles.com, pp. 1-3.
Ford Motor Company, "SYNC with Navigation System," Owner's Guide Supplement, SYNC System Version 1 (Jul. 2007).
Ford Motor Company, "SYNC," Owner's Guide Supplement, SYNC System Version 1 (Nov. 2007).
Ford Motor Company, "SYNC with Navigation System," Owner's Guide Supplement, SYNC System Version 2 (Oct. 2008).
Ford Motor Company, "SYNC," Owner's Guide Supplement, SYNC System Version 2 (Oct. 2008).
Ford Motor Company, "SYNC with Navigation System," Owner's Guide Supplement, SYNC System Version 3 (Jul. 2009).
Ford Motor Company, "SYNC," Owner's Guide Supplement, SYNC System Version 3 (Aug. 2009).
Chinese Patent Office, First Office Action for the corresponding Chinese Patent Application No. 201110352827.5 mailed Nov. 26, 2014.

* cited by examiner

VEHICLE SYSTEM REACTION TO MEDICAL CONDITIONS

CROSS-REFERENCE TO RELATED APPLICATIONS

This application is a continuation of U.S. application Ser. No. 12/941,483 filed Nov. 8, 2010, now U.S. Pat. No. 8,704,669, the disclosure of which is hereby incorporated in its entirety by reference herein.

BACKGROUND

The illustrative embodiments generally relate to a vehicle computing system reacting to detected or input medical conditions.

Heart attacks, seizures, even a lapse into unconsciousness due to, for example, dehydration or choking, can occur at unexpected moments. In fact, these events are typified by such unplanned incidences, with typically little to no forewarning. In addition to these extreme examples, a variety of medical emergencies or conditions can arise at any time.

If a person suffering from a condition that would benefit from, if not require, medical assistance, becomes symptomatic in the presence of another party capable of providing, or at least contacting medical help, undesired eventualities can often be avoided. Severe allergy attacks can be met with antihistamines or steroid shots. A lapse into unconsciousness can be addressed with resuscitation, or prevented entirely with swift assistance. Heart attacks can be quickly responded to by EMS, and seizure victims can be helped to prevent injury to themselves until the seizure passes.

If these conditions arise while a person is alone, however, the consequences may be much more dire. Permanent injury or even death may result. Additionally, if these conditions arise while driving a motor vehicle, especially if the driver is alone, serious injury may result from an accident caused by the onset of the condition, even if the condition itself would not have resulted in injury.

Some emergency conditions come upon a victim so suddenly that no preventative measure can be taken. Many emergency conditions, however, can be projected as a possible consequence of a known medical condition. Further, especially when the medical condition is known, there are often a few minutes or more of symptoms leading up to the onset of an emergency event.

If the window in which symptoms occurs is small, the sufferer may have only a brief period of time in which to react. This may result in a call to 911, a call to a trusted friend or relative, or a call to a doctor. With the exception of 911, which is hopefully always available, any other party contacted my not be available, or may not be able to help. With only potentially minutes to respond to a potentially fatal condition, a patient cannot afford to place unanswered call after unanswered call.

Further, even if the patient is successful in reaching a 911 operator, an ambulance or other EMS may not be in an ideal position to respond. Or, the call to 911 may not have been needed, and thus a valuable and finite medical resource is being improperly utilized. Unfortunately, a person suffering from an apparent emergency condition is not always in a position to make a determination as to whether or not a call to 911 is needed. Even though it is advisable to err on the side of caution in such an instance, many people may over-react to non-threatening conditions.

It may also actually be faster for a person to report to a hospital or care-provider themselves, especially if they are already in a vehicle, than to wait for an ambulance, assuming that the safe transportation services of an ambulance driver are not required. Of course, if the person does not know that the closest hospital/pharmacy/care provider is only a few miles away, that person is likely to opt to wait for EMS to arrive, even if the EMS may take a much longer time to arrive than would the drive to the care provider. This consideration may be particularly relevant in the case that a second party is present in a vehicle and is capable of transporting the patient without an imminent risk of the driver becoming unconscious or otherwise incapable of operating the vehicle.

SUMMARY

In a first illustrative embodiment, a computer-implemented method includes registering, via a vehicle computing system (VCS) included in a vehicle, at least one medical condition associated with a vehicle occupant. The illustrative method also includes monitoring environmental conditions, via the VCS, for the onset of a trigger likely to cause complications with regards to the medical condition.

The illustrative method further includes warning the vehicle occupant, via the VCS, about the onset of the trigger. Finally, the illustrative method includes adjusting a vehicle component or system, via the VCS, in response to the onset of the trigger.

In a second illustrative embodiment, a computer-implemented method includes providing an input to a vehicle computing system (VCS), the input allowing a vehicle occupant to input a medical condition or symptom. The illustrative method also includes receiving an input to the VCS corresponding to a medical condition or symptom.

The illustrative method further includes comparing, via the VCS, the input condition or symptom to a list of known conditions and symptoms and providing via the VCS, medical information regarding the condition or symptom.

The illustrative method additionally includes receiving via the VCS, input indicating whether the condition or symptom is a current condition or symptom. This illustrative method also includes providing recommended medical assistance information to address the condition or symptom, if the condition or symptom is a current condition or symptom via the VCS.

The illustrative method further includes determining if the condition or symptom is a critical condition or symptom, based at least in part on information stored in conjunction with the list of known conditions and symptoms. The illustrative method additionally includes providing emergency medical contact information, including at least one of an option to immediately dial an emergency operator through the VCS or a local medical care provider within close proximity to current GPS coordinates of a vehicle in which the VCS is included, if the condition is a critical condition or symptom.

In a third illustrative embodiment, a vehicle computing apparatus (VCA) includes registering programmed logic circuitry to register at least one medical condition associated with a vehicle occupant. The illustrative apparatus also includes monitoring programmed logic circuitry to monitor environmental conditions, for the onset of a trigger likely to cause complications with regards to the medical condition. The illustrative apparatus additionally includes warning programmed logic circuitry to warn the vehicle occupant about the onset of the trigger. The illustrative apparatus additionally includes adjusting programmed logic circuitry to adjust a vehicle component or system in response to the onset of the trigger.

DETAILED DESCRIPTION

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

Although the following describes the invention in terms of illustrative embodiments, these examples are provided for non-limiting illustrative purposes only, and are not intended to limit the scope of the invention thereto.

Figure 1:
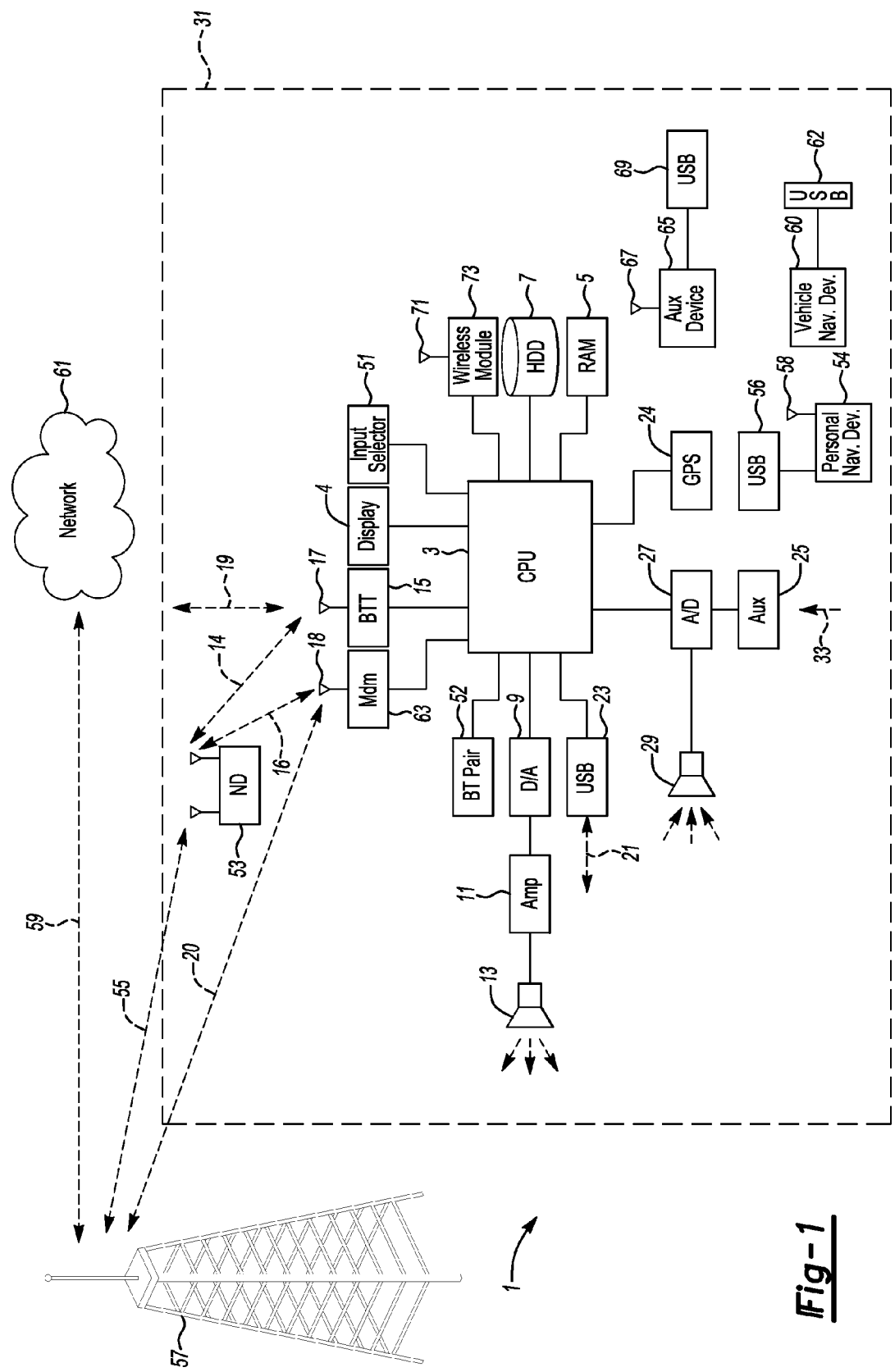
FIG. 1 shows an illustrative example of a vehicle computing system.

FIG. 1 illustrates an example block topology for a vehicle based computing system 1 (VCS) for a vehicle 31. An example of such a vehicle-based computing system 1 is the SYNC system manufactured by THE FORD MOTOR COMPANY. A vehicle enabled with a vehicle-based computing system may contain a visual front end interface 4 located in the vehicle. The user may also be able to interact with the interface if it is provided, for example, with a touch sensitive screen. In another illustrative embodiment, the interaction occurs through, button presses, audible speech and speech synthesis.

In the illustrative embodiment 1 shown in FIG. 1, a processor 3 controls at least some portion of the operation of the vehicle-based computing system. Provided within the vehicle, the processor allows onboard processing of commands and routines. Further, the processor is connected to both non-persistent 5 and persistent storage 7. In this illustrative embodiment, the non-persistent storage is random access memory (RAM) and the persistent storage is a hard disk drive (HDD) or flash memory.

The processor is also provided with a number of different inputs allowing the user to interface with the processor. In this illustrative embodiment, a microphone 29, an auxiliary input 25 (for input 33), a USB input 23, a GPS input 24 and a BLUETOOTH input 15 are all provided. An input selector 51 is also provided, to allow a user to swap between various inputs. Input to both the microphone and the auxiliary connector is converted from analog to digital by a converter 27 before being passed to the processor. Although not shown, numerous of the vehicle components and auxiliary components in communication with the VCS may use a vehicle network (such as, but not limited to, a CAN bus) to pass data to and from the VCS (or components thereof).

Outputs to the system can include, but are not limited to, a visual display 4 and a speaker 13 or stereo system output. The speaker is connected to an amplifier 11 and receives its signal from the processor 3 through a digital-to-analog converter 9. Output can also be made to a remote BLUETOOTH device such as PND 54 or a USB device such as vehicle navigation device 60 along the bi-directional data streams shown at 19 and 21 respectively.

In one illustrative embodiment, the system 1 uses the BLUETOOTH transceiver 15 to communicate 17 with a user's nomadic device 53 (e.g., cell phone, smart phone, PDA, or any other device having wireless remote network connectivity). The nomadic device can then be used to communicate 59 with a network 61 outside the vehicle 31 through, for example, communication 55 with a cellular tower 57. In some embodiments, tower 57 may be a WiFi access point.

Exemplary communication between the nomadic device and the BLUETOOTH transceiver is represented by signal 14.

Pairing a nomadic device 53 and the BLUETOOTH transceiver 15 can be instructed through a button 52 or similar input. Accordingly, the CPU is instructed that the onboard BLUETOOTH transceiver will be paired with a BLUETOOTH transceiver in a nomadic device.

Data may be communicated between CPU 3 and network 61 utilizing, for example, a data-plan, data over voice, or DTMF tones associated with nomadic device 53. Alternatively, it may be desirable to include an onboard modem 63 having antenna 18 in order to communicate 16 data between CPU 3 and network 61 over the voice band. The nomadic device 53 can then be used to communicate 59 with a network 61 outside the vehicle 31 through, for example, communication 55 with a cellular tower 57. In some embodiments, the modem 63 may establish communication 20 with the tower 57 for communicating with network 61. As a non-limiting example, modem 63 may be a USB cellular modem and communication 20 may be cellular communication.

In one illustrative embodiment, the processor is provided with an operating system including an API to communicate with modem application software. The modem application software may access an embedded module or firmware on the BLUETOOTH transceiver to complete wireless communication with a remote BLUETOOTH transceiver (such as that found in a nomadic device).

In another embodiment, nomadic device 53 includes a modem for voice band or broadband data communication. In the data-over-voice embodiment, a technique known as frequency division multiplexing may be implemented when the owner of the nomadic device can talk over the device while data is being transferred. At other times, when the owner is not using the device, the data transfer can use the whole bandwidth (300 Hz to 3.4 kHz in one example).

If the user has a data-plan associated with the nomadic device, it is possible that the data-plan allows for broad-band transmission and the system could use a much wider bandwidth (speeding up data transfer). In still another embodiment, nomadic device 53 is replaced with a cellular communication device (not shown) that is installed to vehicle 31. In yet another embodiment, the ND 53 may be a wireless local area network (LAN) device capable of communication over, for example (and without limitation), an 802.11g network (i.e., WiFi) or a WiMax network.

In one embodiment, incoming data can be passed through the nomadic device via a data-over-voice or data-plan, through the onboard BLUETOOTH transceiver and into the vehicle's internal processor 3. In the case of certain temporary data, for example, the data can be stored on the HDD or other storage media 7 until such time as the data is no longer needed.

Additional sources that may interface with the vehicle include a personal navigation device 54, having, for example, a USB connection 56 and/or an antenna 58; or a vehicle navigation device 60, having a USB 62 or other connection, an onboard GPS device 24, or remote navigation system (not shown) having connectivity to network 61.

Further, the CPU could be in communication with a variety of other auxiliary devices 65. These devices can be connected through a wireless 67 or wired 69 connection. Also, or alternatively, the CPU could be connected to a vehicle based wireless router 73, using for example a WiFi 71 transceiver. This could allow the CPU to connect to remote networks in range of the local router 73. Auxiliary device 65 may include, but are not limited to, personal media players, wireless health devices, portable computers, and the like.

In the illustrative embodiments, a vehicle computing system is capable of being "aware" of various medical conditions of the occupants, and to respond accordingly when an environmental or detected medical condition may impact those occupant's health.

Additionally, the vehicle computing system may responsively answer queries about particular symptoms input thereto, including providing warnings about necessity of imminent care, or advice about a service provider or other place of business that may provide a solution to a problem or projected problem.

In one illustrative example, a person recognizes an onset of, or an existing symptom in themselves or another passenger. Because this embodiment provides access to a medical database, through, for example, but not limited to, a remote connection, it is possible to diagnose a variety of conditions using the latest medical knowledge.

In this embodiment, the passenger or patient will first enter a medical condition—such as diabetes, into a database entry screen. Alternatively, the enterer may elect to speak the condition if no visual display is available or easily interacted with.

If the enterer does not know what medical condition corresponds to an occurring symptom, the enterer can instead elect to input the symptom. In another illustrative embodiment, the enterer may elect a portion of the body that is suffering, and be provided with a list of common symptoms, in case that person cannot adequately describe as input the occurring symptom.

Once the condition/symptom is input, a brief diagnosis may be made, or further questions may be asked to evaluate the symptom. It may be preferable to err on the side of caution, and one precautionary measure may include the display (or available audio input of) a "call 911" option during the entire display/menu interaction.

Once a condition has been reasonably diagnosed, the system may provide a recommended option or action. For example, the system may recommend or offer the option to visit a care provider or source of medical supplies. Additionally or alternatively, if a situation is critical, the system may offer the option to visit or contact an emergency care provider.

In another illustrative embodiment, the vehicle computing system may be aware of existing medical conditions pertaining to occupants of the vehicle. This information may be input on a trip by trip basis, or may be retrieved from a medical profile (local or remote) associated with a vehicle occupant.

In an instance such as this, the computing system may detect the onset or likely onset of a symptom. For example, in one illustrative embodiment, the vehicle computing system may detect the imminent onset of an environmental condition, such as pollen, extreme cold, etc, that may be detrimental to a vehicle occupant. In another example, the system may detect the imminence of a condition based on incoming data from a connected medical monitoring device.

In either event, the system may take action or recommend action to counteract the onset of the condition. In the case of an environmental condition, the vehicle computing system may offer to use vehicle systems to offset the predicted environmental condition. In the case of a predicted medical emergency, the system may project imminent symptoms and, in the event these symptoms occur, offer medical advice to aid in the treatment or addressing of the symptoms or likely to occur emergency condition.

Figure 2:
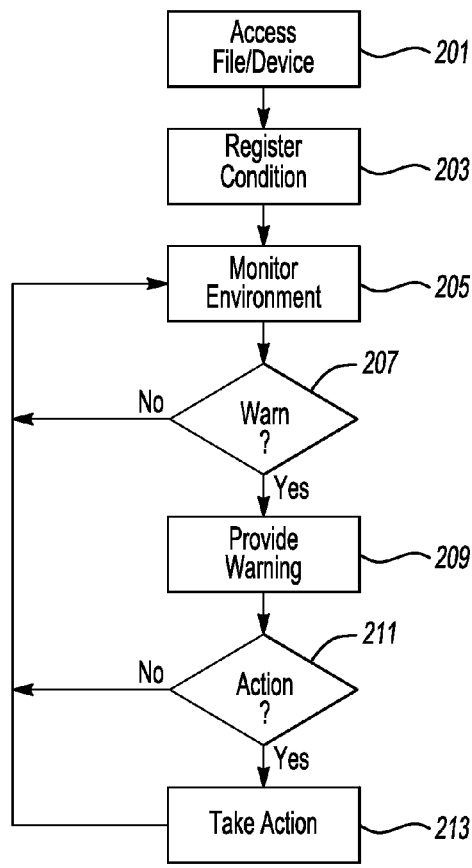
FIG. 2 shows an illustrative example of a process for monitoring a medical device.

FIG. 2 shows an illustrative example of a process for monitoring a medical device. In this illustrative embodiment, the vehicle computing system accesses an account associated with a vehicle occupant, and/or a medical device associated with a vehicle occupant 201.

Based on information obtained from a profile and/or medical devices connected to a vehicle computing system, the vehicle computing system registers one or more conditions which are to be monitored 203. These conditions could be general conditions, symptoms, or environmental elements that may affect or cause an onset of symptoms.

Once the conditions have been registered, the system monitors the passengers and environment for the existence of the registered conditions 205. This monitoring may be done by, for example, vehicle sensors, connections to medical devices, or connections to remote information provision systems that may provide condition information.

If the onset of a condition that is being monitored is detected, the system determines whether or not a warning is appropriate 207. For example, if a potentially adverse environmental condition is detected, the vehicle computing system may warn the occupants of the detected condition. Similarly, if the onset of a potential emergency condition, through the development of, or build up of factors likely to lead to adverse symptoms is detected, the vehicle computing system may similarly warn the occupant(s) 209.

Additionally or alternatively, the vehicle may be programmed to take one or more actions 211 in the event of the onset of an adverse environmental or symptomatic state. For example, the vehicle computing system may reactively activate a vehicle system (HVAC, vehicle lights, nav display with medical provider information, etc) 213, depending on the particulars of a detected medical or environmental condition. One non-limiting example of such an action is described with respect to FIG. 3.

Figure 3:
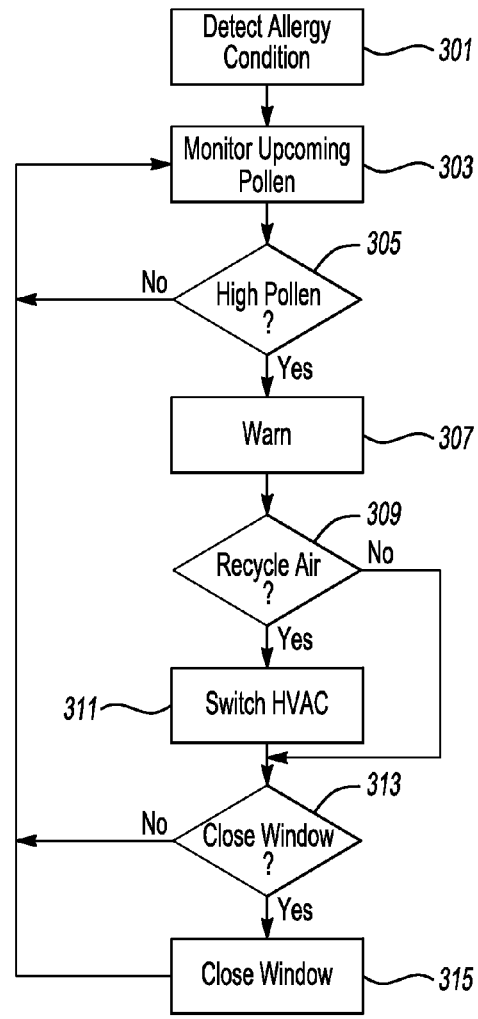
FIG. 3 shows an illustrative example of a process for predicting an imminent symptom onset.

FIG. 3 shows an illustrative example of a process for predicting an imminent symptom onset. In this illustrative embodiment, a vehicle computing system is programmed to reactively adjust a vehicle component, in response to a detected environmental condition that may cause an adverse medical reaction.

For example, without limitation, in this embodiment, the vehicle computing system determines that a passenger (or driver) has an allergic condition that is triggered in the presence of increased pollen 301. By monitoring a remote pollen report 303 (or by having pollen data sent to the vehicle computing system), the vehicle computing system can determine when the pollen count is above an acceptable level, and may further determine if the vehicle is projected to pass into a region where pollen count is high. Both of these determinations may be made at least in part based on the current GPS coordinates of the vehicle, and it may also be useful to include data from a route-planning engine in the case of predictive pollen forecasting.

If a pollen count beyond a tolerable level is not detected or projected to be imminently upcoming 305, the vehicle computing system may simply continue to monitor the pollen without further action.

If, however, the pollen count passes a threshold, the vehicle computing system first issues a warning to the vehicle occupants 307. The warning may simply be a warning about the onset of a high pollen environment, or the warning could include additional information. For example, the warning could recommend that an antihistamine be taken, based on the projected or determined pollen level. The system could further provide the user with a route to a location likely to sell an antihistamine, in the event that the user does not have one handy. This extra information could all be displayed simultaneously, or it could be the result of user selected options. Additionally, the vehicle computing system could output this information in an audible manner.

In this embodiment, two additional actions are associated with a predicted or occurring pollen problem. First, the system may switch to using recycled air 309, if a vehicle HVAC system is currently in operation. The system may either automatically switch to recycled air, or the system may ask the user if the system should switch to recycled air. If the switch is to be made, the vehicle computing system adjusts the current HVAC setting so that recycled air is being used 311.

Additionally or alternatively, the vehicle computing system may ask the user if any open windows should be closed (or automatically close the windows) 313. If the windows are to be closed, the system may automatically enable electric windows to close themselves 315. Additionally, although not shown, if an exterior temperature exceeds a certain threshold, the vehicle computing system may enable the HVAC system if the windows are closed. This could be an automatic action or in response to a user agreeing to this course of action.

Figure 4:
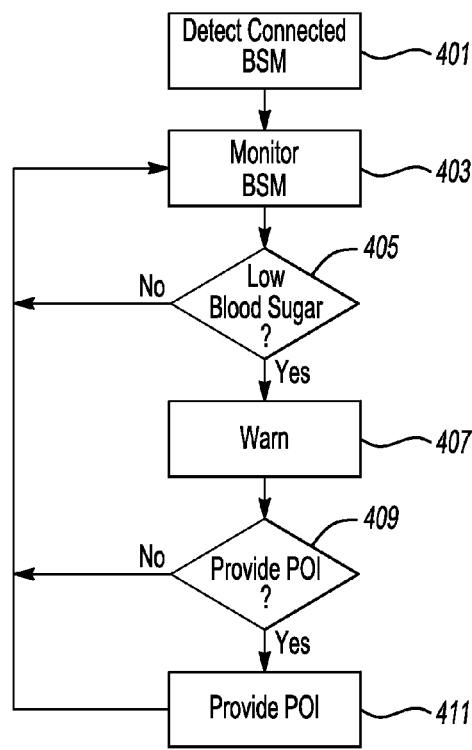
FIG. 4 shows an illustrative example of a process for responding to an alert condition with pertinent information.

FIG. 4 shows an illustrative example of a process for responding to an alert condition with pertinent information. In this illustrative embodiment, a vehicle computing system detects the presence of a blood sugar monitor that is currently monitoring the blood sugar of a vehicle occupant 401. The vehicle computing system connects to the blood sugar monitor and monitors data therefrom 403.

If the blood sugar of the vehicle occupant drops below a threshold level 405, the vehicle computing system will warn the occupant of the condition 407. This may allow the occupant to obtain a source of sugar, and avoid going into anaphylactic shock. The severity of the warning may also increase in proportion to a deficiency in blood sugar levels, and at dangerous levels, emergency medical information (and possibly a "quick 911" option) may also be provided to the occupant.

Further, in this illustrative embodiment, the vehicle computing system may provide a quick access point of interest 411, such as a location where blood sugar could be raised, or the location of a medical provider who can address a critical issue. This option could be provided in response to a user request, or may be automatically provided depending on the severity of the blood sugar deficiency.

Figure 5:
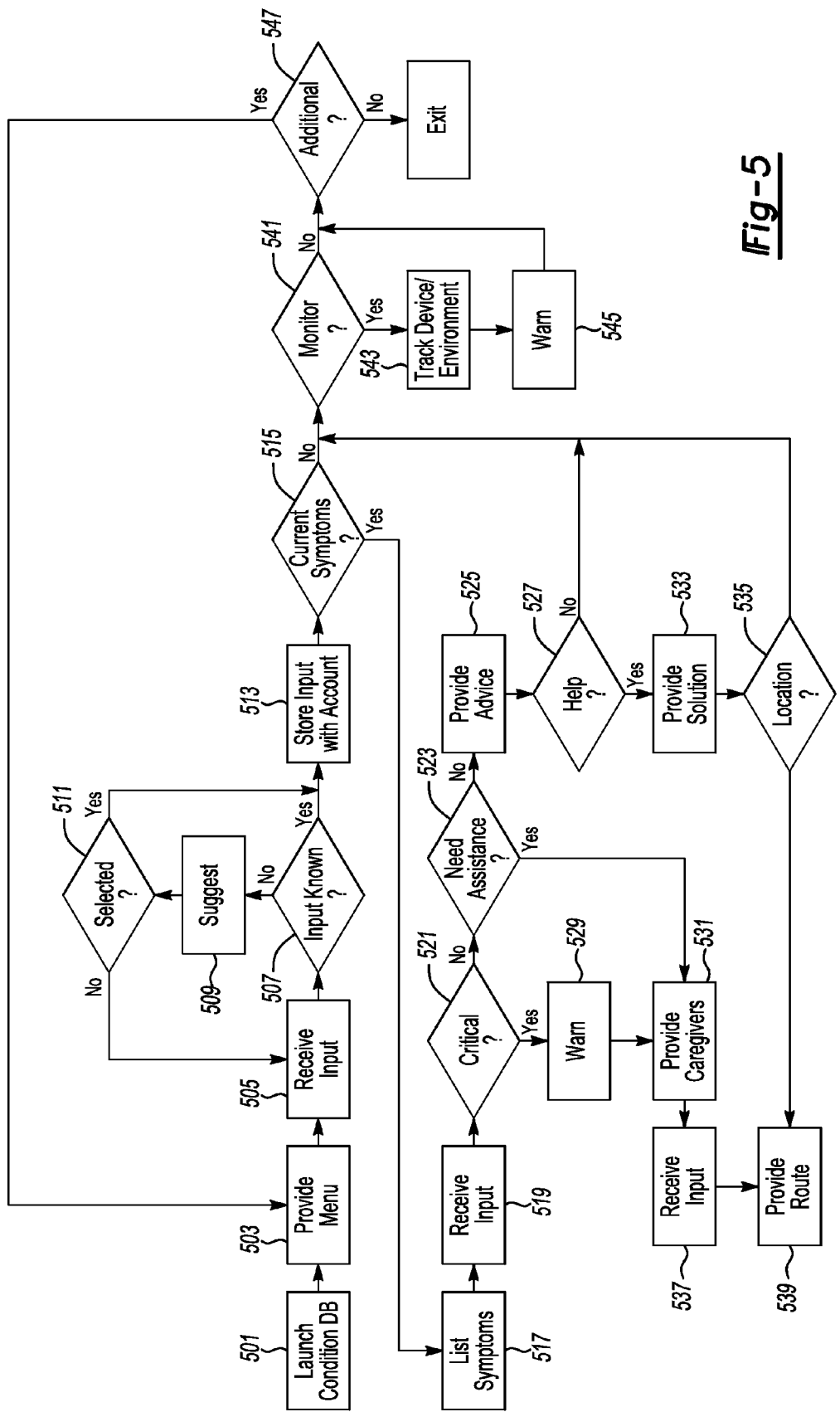
FIG. 5 shows an illustrative example of a symptom analysis database access.

FIG. 5 shows an illustrative example of a symptom analysis database access. In this illustrative embodiment, a passenger uses a medical database to access relevant information about a symptom from which a vehicle occupant may be suffering. The input may be done on a navigation display or through a vehicle microphone. Additionally, if the vehicle computing system is in communication with a wireless device, the input may be done through the screen of the device and relayed to the vehicle computing system.

In this illustrative embodiment, the vehicle computing system first receives a request to launch a medical condition database access application 501. Once the application is initiated, the vehicle computing system provides a menu allowing input of a condition or symptom 503. From this point, the system receives input from an occupant 505. The input could be a medical condition, a medical symptom, or a more generalized request (e.g., without limitation—"headache", "pack pain", etc.).

If the condition is known, the vehicle computing system stores that condition or symptom with an account associated with the occupant for which the request is being made 513. This assumes that the system is capable of such storage, and that an account exists for the particular occupant having the condition or exhibiting the symptom. By storing the information, it can later be transferred to a permanent medical record, provided to a care provider for analysis, and used in later diagnoses without having to be input again.

If the condition/symptom/request is unknown, the system may suggest similar or likely conditions/symptoms 509. If one of these suggestions is accepted/selected 511, the system stores the selected option with the appropriate account.

Once the condition/symptom/request has been input, the system may request to know whether or not this is a condition from which the occupant is currently suffering 515. If the condition is current, and is a critical one, this may allow the system to provide immediate assistance to the occupant.

If the input represents a current state of an occupant, the vehicle computing system, in this embodiment, may list one or more symptoms associated with a condition 517 (assuming, of course, that a condition has been input and not a precise symptom). The system then receives input from the occupant regarding any possible symptoms 519. For example, if the condition was "diabetes" then the symptom may be "light headedness" or "dizziness" or "low blood sugar", etc. If the input symptom represents a critical or possibly critical condition 521 (for example, if the symptom represent a likelihood that the occupant may soon go into shock, unconsciousness, etc), the vehicle computing system may present a warning to the occupant 529.

In addition to the warning, the vehicle computing system may provide one or more caregivers who can address the situation 531. These caregivers could be proximate to the vehicle's current position, and may also be vetted based on insurance information that is known by the vehicle computing system.

For example, if the occupant is in a critical or semi-critical state, the vehicle computing system may find local caregivers and then cross reference that list with preferred providers as can be known from the occupant's insurance information. Both in and out of network caregivers may be provided, with some indication (such as estimated distance or time) as to how far away the caregiver is located. The system may also provide an option, for example, to immediately dial 911 if the condition is serious enough.

In addition to providing directions, the system may provide a contact number for the caregiver and give the occupant the option of calling the caregiver. This may assist in determining the seriousness of the condition and can further inform the caregiver that a patient arrival is imminent.

The occupant can then select a particular caregiver 537 and the vehicle computing system will provide routing instructions to that caregiver 539. This should allow the occupant to reach the caregiver in a timely manner.

If the system does not determine that the condition is a "critical" condition, the system may still ask the occupant if medical assistance 523 is desired. If no medical assistance is needed or is believed to be needed, the system may provide advice 525 based on the input information. This could be, for example, advice on how to alleviate a symptom, or could be advice that recommends medical assistance if X or Y symptom persists or occurs.

If, after reading the advice, the occupant determines that help or further assistance is needed 527, the vehicle computing system may provide a solution to a particular problem ("take the following medication," "contact a physician," etc.) 533. If there is a location associated with the advice 535, the system will receive input of a selected location and provide directions.

For example, the vehicle computing system may recommend the ingestion of a particular medicine. Using local pharmacy information, a number of options as to where this medication may be obtained could be provided. The user could then select a particular location and the vehicle would be routed to that location. Again, phone numbers and the option to call the location may also be provided, in case prescription medication is needed, so that the medication may be available by the time the occupant arrives.

If the input condition/symptom/request is not a current state, or if the vehicle is not being routed in response to the state, the vehicle computing system may ask the occupant if the condition should be monitored 541. If desired, the system can monitor the local environment for factors that could affect the condition (e.g., allergies and pollen), it may periodically ask for input on a symptom to determine if the symptom is persisting, worsening, improving, etc., or it may monitor an associated and connected medical or wellness device 543.

If the monitoring detects in a state where the occupant needs to be warned of an imminent emergency or danger, the system can provide an adequate warning 545.

Finally, once the condition is addressed, the system asks the occupant if any additional information is needed or additional symptoms or conditions need to be input 547.

Figure 6:
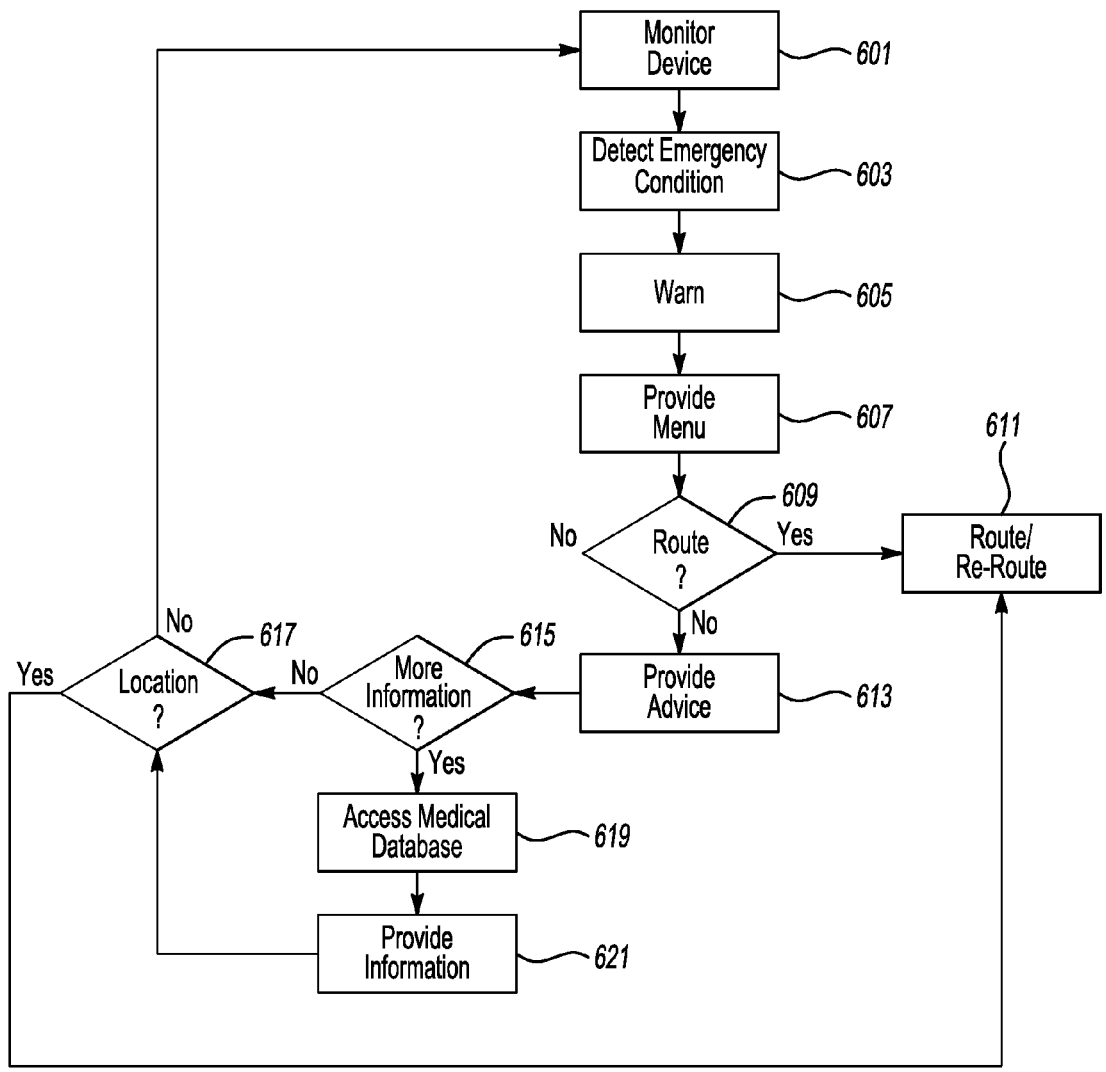
FIG. 6 shows an illustrative example of a process for responding to a potential emergency condition with emergency information.

FIG. 6 shows an illustrative example of a process for responding to a potential emergency condition with emergency information. In this illustrative embodiment, the vehicle computing system monitors an occupant 601 having, for example, an attached medical device. Other monitoring may also be possible. For example, it may be possible, using vehicle systems such as microphones or cameras, to detect an onset of a severe allergic reaction or other condition.

If an emergency condition is detected 603, a warning is provided to the vehicle occupant 605 and a menu of options with more information or other steps to be taken is also provided 607. This may contain, for example, an "quick 911" option (selection of which immediately dials 911), a list of providers or locations where assistance can be had, a corresponding list of phone numbers, one or more known emergency contacts, etc.

If the selected option includes a request to travel to a location 609, the vehicle computing system routes the vehicle to the selected location 611. Otherwise, the system provides a solution in conjunction with the requested information (dials a number, brings up symptom information, etc) 613.

Once the initial solution has been provided, the vehicle computing system may ask the occupant if more information is required 615. If no more information is needed, and the requested solution included a location to which the vehicle had not yet been routed 617, the system may route the vehicle to the location 611.

If more information is required, the system may access, for example, a medical database 621 and provide information on the condition or symptom that was detected at the initiation of the process 623.

Although the invention has been described with reference to illustrative embodiments, these embodiments were provided for exemplary purposes only, and are not intended to limit the scope of the invention to the disclosed examples.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A system comprising:
a processor configured to:
receive occupant input of a symptom;
determine that the symptom corresponds to a critical medical state of a known occupant medical condition;
based on the critical medical state, present a user selectable option to dial emergency services;
receive selection of the option to dial emergency services; and
place a call to emergency services in accordance with the selection.

2. The system of claim 1, wherein the medical condition corresponds to information previously saved with respect to the vehicle occupant.

3. The system of claim 1, wherein the processor is configured to present an option to call a caregiver, proximate to a vehicle location, known to provide care for the known medical condition.

4. The system of claim 3, wherein the processor is configured to present a selectable option to route to the caregiver and to provide routing to the caregiver upon selection of the option.

5. A computer-implemented method comprising:
receiving occupant input of a symptom;
determining that the symptom corresponds to a critical medical state of a known occupant medical condition;
based on the critical medical state, presenting a user selectable option to dial emergency services;
receiving selection of the option to dial emergency services; and
placing a call to emergency services in accordance with the selection.

6. The method of claim 5, wherein the medical condition corresponds to information previously saved with respect to the vehicle occupant.

7. The method of claim 5, further comprising presenting an option to call a caregiver, proximate to a vehicle location, known to provide care for the known medical condition.

8. The method of claim 7, further comprising presenting a selectable option to route to the caregiver and routing to the caregiver upon selection of the option.

9. A non-transitory computer-readable storage medium, storing instructions that, when executed by a processor, cause the processor to perform a method comprising:
receiving occupant input of a symptom;
determining that the symptom corresponds to a critical medical state of a known occupant medical condition;
based on the critical medical state, presenting a user selectable option to dial emergency services;

receiving selection of the option to dial emergency services; and placing a call to emergency services in accordance with the selection.

10. The storage medium of claim 9, further comprising presenting an option to call a caregiver, proximate to a vehicle location, known to provide care for the known medical condition.

11. The storage medium of claim 10, further comprising presenting a selectable option to route to the caregiver and routing to the caregiver upon selection of the option.

* * * * *